United States Patent [19]

Mandecki

[11] Patent Number: 6,046,003
[45] Date of Patent: *Apr. 4, 2000

[54] METHOD OF DETERMINING THE SEQUENCE OF NUCLEIC ACIDS EMPLOYING SOLID-PHASE PARTICLES CARRYING TRANSPONDERS

[75] Inventor: Wlodek Mandecki, Libertyville, Ill.

[73] Assignee: Pharmaseq, Inc., Monmouth Junction, N.J.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/013,114

[22] Filed: Jan. 26, 1998

Related U.S. Application Data

[62] Division of application No. 08/564,860, Nov. 30, 1995, Pat. No. 5,736,332.

[51] Int. Cl.$^7$ .......................... G05B 23/02; G08C 19/12; C07H 21/04; C12Q 1/68
[52] U.S. Cl. .................. 435/6; 340/825.54; 340/870.17; 340/825.06; 435/91.2; 435/810; 435/973; 436/501; 436/519; 436/520; 536/23.1; 536/24.3
[58] Field of Search ........................... 435/6, 91.2, 810, 435/973; 340/825.06, 825.54, 870.17; 436/501, 520, 519; 536/23.1, 24.3

[56] References Cited

U.S. PATENT DOCUMENTS

| | | | |
|---|---|---|---|
| 4,177,253 | 12/1979 | Davies et al. | 424/1 |
| 4,297,337 | 10/1981 | Mansfield et al. | 424/1 |
| 4,452,773 | 6/1984 | Molday | 424/1 |
| 4,454,234 | 6/1984 | Czerlinski | 436/526 |
| 4,556,883 | 12/1985 | Strietzel | 340/825.54 |
| 4,672,040 | 6/1987 | Josephson | 436/526 |
| 4,777,145 | 10/1988 | Luotola et al. | 436/526 |
| 4,778,769 | 10/1988 | Forrest et al. | 436/501 |
| 4,822,566 | 4/1989 | Newman | 422/68 |
| 4,857,893 | 8/1989 | Carroll | 340/572 |
| 4,923,819 | 5/1990 | Fernandez et al. | 455/41 |
| 4,941,201 | 7/1990 | Davis | 455/6 |
| 4,965,188 | 10/1990 | Mullis et al. | 340/433 |
| 5,019,815 | 5/1991 | Lemelson et al. | 422/52.02 |
| 5,034,192 | 7/1991 | Wrighton et al. | 340/825.56 |
| 5,071,774 | 12/1991 | Vorpahl et al. | 204/403 |
| 5,153,583 | 10/1992 | Murdoch | 435/6 |
| 5,200,051 | 4/1993 | Cozzette et al. | 340/572 |
| 5,202,231 | 4/1993 | Drmanac et al. | 340/572 |
| 5,214,409 | 5/1993 | Beigel | 340/825.54 |
| 5,218,343 | 6/1993 | Stobbe et al. | 340/825.54 |
| 5,223,851 | 6/1993 | Hadden et al. | 343/873 |
| 5,235,326 | 8/1993 | Beigel et al. | 340/825.54 |
| 5,245,332 | 9/1993 | Katzenstein | 340/825.54 |
| 5,250,944 | 10/1993 | Urbas et al. | 340/870.12 |
| 5,252,962 | 10/1993 | Urbas et al. | 340/570.17 |
| 5,257,011 | 10/1993 | Beigel | 340/572 |
| 5,262,772 | 11/1993 | Urbas et al. | 340/825.54 |
| 5,266,926 | 11/1993 | Beigel | 340/52 |
| 5,284,748 | 2/1994 | Mroczkowski et al. | 435/6 |
| 5,347,263 | 9/1994 | Carroll et al. | 340/572 |
| 5,422,636 | 6/1995 | Urbas et al. | 340/825.54 |
| 5,440,300 | 8/1995 | Spillman, Jr. | 340/825.54 |
| 5,445,970 | 8/1995 | Rohr | 436/526 |
| 5,466,348 | 11/1995 | Holm-Kennedy | 204/153.1 |
| 5,481,262 | 1/1996 | Urbas et al. | 340/870.17 |
| 5,491,097 | 2/1996 | Ribi et al. | 436/516 |
| 5,492,806 | 2/1996 | Drmanac et al. | 435/6 |
| 5,525,464 | 6/1996 | Drmanac et al. | 435/6 |
| 5,552,270 | 9/1996 | Khrapko et al. | 435/6 |
| 5,641,634 | 6/1997 | Mandecki | 435/6 |
| 5,736,332 | 4/1998 | Manecki | 435/6 |

FOREIGN PATENT DOCUMENTS

| | | |
|---|---|---|
| 0526173 A2 | 2/1993 | European Pat. Off. . |
| WO90/13666 | 11/1990 | WIPO . |
| WO93/04199 | 3/1993 | WIPO . |
| WO93/21340 | 10/1993 | WIPO . |
| WO96/36436 | 11/1996 | WIPO . |
| WO97/19958 | 6/1997 | WIPO . |
| WO97/20073 | 6/1997 | WIPO . |
| WO97/20074 | 6/1997 | WIPO . |

OTHER PUBLICATIONS

Nicolaou et al, "Radiofrequency encoded combinatorial chemistry", Angeew. Chem. Int. Ed. Engl. 34(20):2289–2291, 1995.

Moran et al, "Radio frequency tag encoded combinatorial library method for the discovery of tripeptide substituted cinnamic acid inhibitors of the protein tyrosine phosphatase PTP1B", J. Am. Chem. Soc. 117:10787–10788, 1995.

*The Chemical Factory: An Assembly–Line Approach To Automated Combinatorial Chemistry On Solid Phase*, Author(s): John F. Cargill and Barry E Toyonaga.

*Principles And Practice Of Immunoassay*, Chapter 5, "Immunoassay Design And Optimization".

*Principles And Practice Of Immunoassay*, Chapter 13, "Heterogenous Fluoroimmunoassay."

*Enzyme Immunodiagnosis*, Author(s):Edouard Kurstak, 1986.

Albretsen, C. et al., "Applications of magnetic beads with covalently attached oligonucleotides in hybridization: Isolation and detection of specific measles virus mRNA from a crude cell lysate" *Analytical Biochemistry* (1990) vol. 189, pp. 40–50.

(List continued on next page.)

*Primary Examiner*—Jeffrey Fredman
*Attorney, Agent, or Firm*—Brinks Hofer Gilson & Lione

[57] ABSTRACT

A method is described for determining the sequence of nucleic acids. The method employs small solid phase particles having transponders, with a primary layer of an oligonucleotide of known sequence attached to the outer surface of the particle. A read/write scanner device is used to encode and decode data on the transponder. The stored data includes the sequence of the oligonucleotide immobilized on the transponder. The sequence of sample nucleic acids is determined by detecting annealing to an oligonucleotide bound to a particle, followed by decoding the transponder to determine the sequence of the oligonucleotide.

16 Claims, 7 Drawing Sheets

OTHER PUBLICATIONS

Alper, J. "Drug Discovery on the assembly line" *Science* (Jun. 3, 1994) vol. 264, pp. 1399–1401.

Atkinson, T. et al., "A convenient procedure for the synthesis of oligodeoxyribonucleotide affinity columns for the isolation of mRNA" *Nucleic Acids Research,* (1988), vol.16, No. 13.

Cargill, JF and BE Toyonaga. *The Chemical Factory: An Assembly Line Approach to Automated Combinatorial Chemistry on Solid Phase.*

Caruthers, MH et al., "Deoxyoligonucleotide synthesis via the phosphoramidite method" *Gene Amplification and Analysis,* vol. III, (TS Papas et al., eds.) Elsevier Press, Amsterdam.

Drmanac, R et al., "DNA sequence determination by hybridization: a strategy for efficient large–scale sequencing." *Science* (1993) vol. 260, pp. 1649–1652.

Fiore, F et al., "The Abbott IMx Automated Benchtop Immunochemistry Analyzer System" *Clinical Chemistry* (1998) vol. 34, No. 9.

Ghosh, SS and GF Musso. "Covalent attachment of oligonucleotides to solid supports" *Nucleic Acids Research,* (1987) vol. 15, No. 13.

Gingeras TR et al., "Hybridization properties of immobilized nucleic acids" *Nucleic Acids Research* (1987) vol. 15, No. 13.

Hooft van Hujisduijnen, RAM et al. "A means to reduce the complexity of oligonucleotides encoding degenerate peptides" *Nucleic Acids Research* (1992) Vol. 20, No. 4.

Hultman et al., "Direct solid phase sequencing of genomic DNA using magnetic beads as solid support" *Nucleic Acids Research* (1989) vol. 17, No. 13, pp. 4937–4946.

Ihalainen et al. *Biotechniques* (1994) vol. 16, pp. 938–943.

Lam, KS et al., "A new type of synthetic peptide library for identifying ligand–binding activity" *Nature* (Nov. 7, 1991) vol. 354, pp. 82–84.

Maskos E. et al. "Oligonucleotide hybridisations [sic ]properties of oligonucleotides synthesized *in situ*" *Nucleic Acids Research* (1992) vol. 20, No. 7, pp. 1679–1684.

McHugh, T. "Flow Microsphere Immunoassay for the Quantitative and Simultaneous Detection of Multiple Soluble Analytes" *Methods in Cell Biology* (1990) vol. 42, pp. 575–595.

Mirzabekov, AD. "DNA sequencing by hybridization—a megasequencing method and a diagnostic tool" *Tibtech* (1994) vol. 12.

Moran et al. "Radio frequency tag encoded combinatorial library method for the discovery of tripeptide–substituted cinnamic acid inhibitors of the protein tyrosine phosphatase PTP1B" *J. Am. Chem Soc.* (1995) vol. 117, pp. 10787–10788.

Morrissey, NE et al. "Modified method for determining carcinoembryonic antigen in the presence of human anti––murine antibodies" *Clinical Chemistry* (1993) vol. 39, No. 3.

Nicolaou et al. "Radiofrequency encoded combinatorial chemistry" *Angew. Chem Int. Ed.* (1995), vol. 34, No. 210, pp. 2289–2291.

Pease, Ac et al., "Light–generated oligonucleotide arrays for rapid DNA sequence analysis" *Proc. Natl. Acad. Sci.* (1994), vol. 91, pp. 5022–5026.

Pierce catalog. (1994) pp. T159, T314–T315, Rockford, Illinois US.

*Principles And Practice Of Immunoassay,* Chapter 5, "Immunoassay Design And Optimization".

*Principles And Practice Of Immunoassay,* Chapter 13, "Heterogeneous Fluoroimmunoassay".

Sambrook et al. *Molecular Cloning: A laboratory manual* (1989) $2^{nd}$ ed. Lake Press, NY.

Service, R. "Radio tags speed compound synthesis" *Science,* (Oct. 27, 1995) vol. 270, pp. 577.

Sproat, BS and DM Brown "A new linkage for solid phase synthesis of oligodeoxyribonucleotides" *Nucleic Acids Research* (1985) vol. 13, pp. 2979–2987.

Urdea et al. "A comparison of non–radioisotopic hybridization assay methods using flouroscent, chemiluminescent and enzyme labeled synthelic oligodeoxyribonucleotide probes" *Nucleic Acids Research,* (1988) vol. 16, No. 11 pp. 4937–4956.

METHOD OF DETERMINING THE SEQUENCE OF NUCLEIC ACIDS EMPLOYING SOLID-PHASE PARTICLES CARRYING TRANSPONDERS

This application is a divisional of application Ser. No. 08/564,860, filed Nov. 30, 1995, now U.S. Pat. No. 5,736, 332.

BACKGROUND OF THE INVENTION

This invention relates to materials and methods for determining the sequence of unknown or target nucleic acids, and more specifically to materials and methods for determining the sequence of target nucleic acids using an electronically-indexed solid phase, with transponders associated with the solid phase particles.

A high throughput method for ascertaining the sequence of sample nucleic acids is sequencing by hybridization (SBH). In that method, a large number of oligonucleotide probes is allowed to interact with the nucleic acid molecules in a sample, and a detection system is provided to determine whether individual oligonucleotides have annealed to the template. Two basic designs have been described. In one, the oligonucleotide probes are arranged in a two-dimensional array on the surface of a membrane, filter, VLSI chip, or the like. In the other, the array on the membrane is formed with a large number of sample DNA sequences, and each membrane is subjected to a series of hybridization steps with different oligonucleotide probes. A label used to monitor the binding, either a radioactive isotope or a fluorophore, is carried on the sample DNA or on the oligonucleotide probe. The sequence is derived from coordinates of spots showing a high level of the label deposition on the two-dimensional arrays.

Conventional SBH methods are limited by difficulties related to preparation of arrays of DNA, non-specific annealing of DNAs, the need for special instrumentation to read the data and the automation of the process and data analysis. In SBH, the sequence is determined by defining the two-dimensional coordinates of relevant dots in the array formed by the deposited DNA molecules. In the present invention, a partial or the complete sequence of the DNA molecule is determined by decoding the electronic memory elements associated with DNA probes of known sequence.

An advantage of the present invention over conventional sequencing methods is that it is extremely fast, because the sequence is deduced from a series of readings of digitally-stored sequences in the transponder, rather than from a series of measurements of a chemical or physical property of DNA, or the location of DNA in an array. The method of this invention is referred to hereinafter as digital sequencing.

SUMMARY OF THE INVENTION

The present invention overcomes the problems of conventional sequencing methods by employing solid phase particles having a transponder associated with each particle. The particles carry oligonucleotide probes attached to their surface, and the sequence of the oligonucleotide is encoded on a memory element on the transponder. The oligonucleotide probes correspond to subsequences believed to exist in the target sequence.

To determine the sequence of sample, or "target" DNA, the target DNA of unknown sequence is labeled with a fluorophore and combined with transponder particles carrying known oligonucleotides under annealing conditions. The transponders are analyzed to detect the fluorescence or color originating from a label that indicates that target DNA has bound to the probe attached to the surface of the transponder, and the information stored electronically in the transponder is decoded. Dedicated sequence analysis software may then be used to determine the complete or partial sequence of the DNA target.

In one aspect, the present invention provides a solid phase particle for use in determining the sequence of nucleic acids, comprising a solid phase particle having a transponder, and an oligonucleotide probe having a known sequence attached to an outer surface of the particle.

In another aspect, the present invention provides a method of determining the sequence of sample nucleic acids, comprising the steps of employing solid phase particles with transponders.

In another aspect, the invention provides a kit for determining the sequence of unknown nucleic acids, comprising an assay vessel, and a set of solid phase particles having transponders, and a different oligonucleotide attached to the surface of the probe.

DETAILED DESCRIPTION OF THE INVENTION

Figure 1:
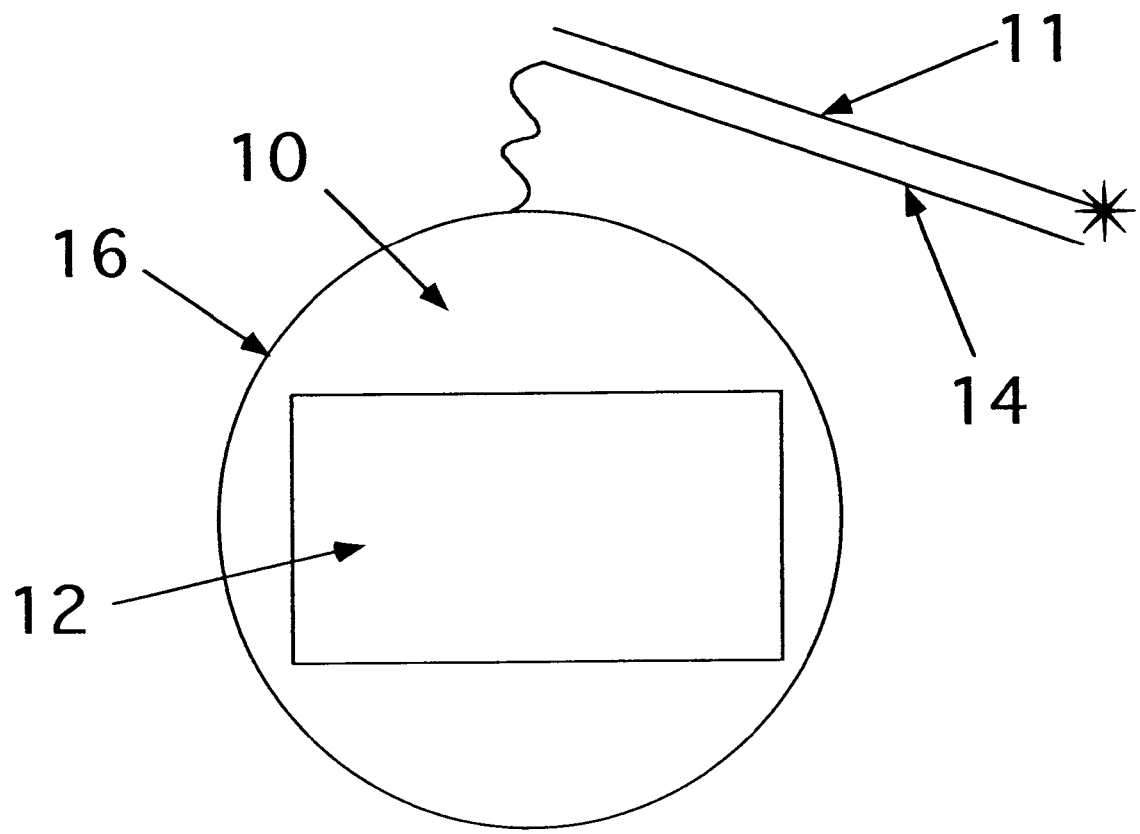
FIG. 1 is a schematic representation of a sequencing procedure of this invention.

FIG. 1 depicts a simple sequencing procedure of the current invention. A solid phase particle 10 with a transponder 12 is derivatized by attaching an oligonucleotide probe 14 of known sequence to the outer surface 16 of the particle 10. The transponder 12 is encoded with an index number that indicates the sequence of the oligonucleotide probe 14. The particle 10 is immersed in a solution containing labelled target DNA 11, and the solution is heated to cause DNA to dissociate, then cooled to allow the DNA to anneal, resulting in target DNA 11 annealing to the probe 14.

The transponder 12 is analyzed to detect the fluorescence of any target DNA 11 bound to the transponder 12, and the transponder 12 is decoded using a read/write scanner device (not shown). In practice a group of transponders, each carrying a different probe and each encoded with the sequence of that probe would be used.

The target DNA is preferably pre-treated by digestion with an appropriate restriction endonuclease, or fragmented by digesting with DNase I, to yield relatively short (preferably 10 nt to 100 nt) preferably single-stranded DNA. Pretreatment may also involve a conversion of DNA to RNA by cloning and in vitro transcription, followed by a partial hydrolysis of RNA (if necessary), or a generation of a DNA fragment by PCR, and the latter can be coupled with labeling of DNA with a fluorophore. DNA provided for sequencing may already be in the preferred form. If, however, the DNA is in the form of a long double-stranded DNA molecule, a long single-stranded DNA molecule, a closed circular DNA molecule, or a nicked circular double-stranded DNA molecule, the DNA must be pre-treated.

Labelling sample DNA with a fluorogenic hapten before annealing is a practical, although not always necessary, step in digital sequencing. Restriction fragments with the 5'-protruding end can be labeled in a chain extension reaction with a DNA polymerase utilizing one or more of dNTPs derivatized with a fluorogenic hapten. 3'-ends of DNA molecules can be labeled in an enzymatic reaction employing a terminal deoxynucleotidyl transferase (TdT) and dNTP derivatized with a fluorogenic hapten. In some sandwich-type applications, the fluorogenic hapten can be replaced with any hapten (e.g. biotin) for which an antibody (or a binding partner) is available, the goal being to detect the binding of labeled DNA to the transponders through a sandwich configuration involving an anti-hapten antibody and a secondary anti-antibody antibody conjugated to an enzyme, said enzyme catalyzing a reaction with a precipitating fluorogenic substrate.

Several types of nucleic acid can be immobilized on the transponders. They include DNA, RNA and modifications thereof, such as protein-nucleic acid (PNA) molecules. It is preferred that the immobilized nucleic acids are single-stranded. The length of the immobilized nucleic acids can vary in different implementations of the digital sequencing, the requirement being that the length should be sufficient to provide a desired level of binding specificity to the target DNA. In one embodiment of this invention, the oligonucleotide probes correspond to subsequences that are believed to exist in the target nucleic acid sequence.

There are several methods to immobilize nucleic acids on the solid phase particles of this invention, including the conjugation of oligonucleotides to the transponders, or the direct chemical synthesis of the oligonucleotide on the transponders. Combinatorial synthesis is a preferred method of direct chemical synthesis, and involves up to four independent condensations of a four different nucleosides (A, C, G and T) on a large number of transponders in four vessels. The transponders are divided into four pools, and each pool is reacted with a different nucleoside. After each condensation, the transponders in the four pools are encoded with a symbol indicating the nucleoside used in the condensation. The four transponder pools are then combined and redistributed into four vessels, and the process is repeated as many times as necessary and practical. The net result of combinatorial synthesis on transponders is that the transponders are derivatized with different oligonucleotides, and the sequence of the oligonucleotide is encoded in the transponder.

The derivatized transponders and the target DNA are kept in a single vessel in an appropriate buffer. The volume of the buffer must be sufficient to completely immerse the transponders in the buffer. An appropriate buffer for the annealing reaction is phosphate-buffered saline (PBS), but many other buffers are suitable, as is well-known by those of ordinary skill in this art. The vessel is heated to a temperature typically in the range of 60°–100° C. The temperature should be sufficient to allow for melting of double-stranded DNA that might exist in the vessel into the single-stranded form. The vessel is then slowly cooled to a temperature below the melting temperature for the sequences immobilized on the transponder, which typically is in the range of 0°–60° C., and is often room temperature. The transponders are then washed thoroughly several times to remove unbound target DNA.

If the target DNA was fluorescence-labeled before annealing, no post-annealing treatment is needed, and the transponders can be subjected to decoding, and the fluorescence of the surface can be measured. Alternatively, if the target DNA was not labeled, fluorescence-labeling must be done after annealing. Either target DNA (associated with the oligonucleotide bound to the transponder) can be labeled, or the oligonucleotide probe on the transponder (but only those that are associated with the target DNA) can be labeled. A method suitable for both approaches is chain extension utilizing a DNA polymerase.

Chain extension labeling procedures can differ with regard to: (a) the type of the fluorophore-tagged nucleotide used for the labeling, or (b) the number of different fluorescent nucleotides used in the extension reaction (choice of the adenine, cytosine, guanine or thymine derivatives). As to the type of nucleotide used, the nucleotide can be either of the deoxy type, or the dideoxy type. More than one labeled deoxy nucleotide can be incorporated into the extended portion of the chain, but the incorporation of only one dideoxy nucleotide is attainable, since it prevents further chain extension.

The labeling can be combined with a fluorescence detection method for transponders which allows for distinguishing the type of the fluorescence label used by identifying the maximum emission wavelength of the fluorophore, similar to the implementation in automated sequencing on Applied Biosystems sequencers. The use of dideoxy nucleotides in digital sequencing, therefore, offers the ability to identify the residue immediately proximal to the 3' end of either target DNA, or the oligonucleotide on the transponder, depending on the approach used.

In a preferred embodiment of the labeling procedure in the presence of four fluorophore-labeled dideoxy nucleotide triphosphates (ddATP,ddCTP,ddGTP and ddTTP) the primers attached to the transponder that annealed to the target are extended by one nucleotide residue by a DNA polymerase. The type of the incorporated residue (A, C, G or T) is determined by the sequence of the target. Therefore, the wavelength at which the maximum intensity of fluorescence is observed indicates the residue type. After the extension step, the particles are passed through a fluorometer capable of discriminating between four wavelengths of emitted light. In this approach, more information is obtained than in the basic implementation of the method. As previously, the presence of the fluorescence is an indication that the annealing took place, but now the wavelength of the fluorescence additionally identifies the target residue that is immediately downstream from the primer (i.e. close to the 3' end of the primer).

In an alternative version of the above procedure, only one fluorophore is used in the reaction, but four separate extension reactions are performed in four separate vessels employing one of four ddNTPs in each vessel. After the reaction and appropriate washes, the particles from the four vessels are mixed together, and the remainder of the procedure is carried through as presented above. In this case, however, an additional encoding step of the particle's memory is needed to provide the information about the type of nucleotide used in the extension reaction for the given transponder.

Figure 2:
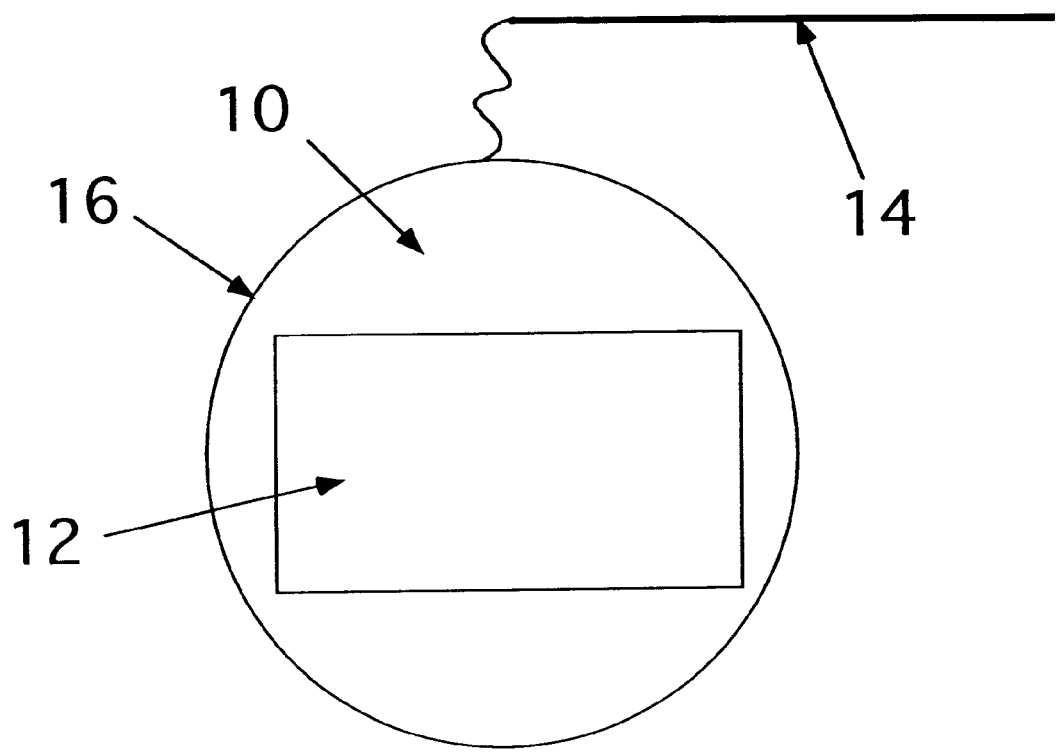
FIG. 2 is a cross-sectional view of a solid phase particle with a transponder, and a primary layer of biomolecules bound to a surface thereof.

FIG. 2 depicts a solid phase particle for use in this invention. The particle 10 is derivatized by attaching an oligonucleotide probe 14 of known sequence to a surface 16 of the particle 10. A transponder 12 is associated with the particle 10. The transponder 12 is encoded with an index number that indicates the sequence of the probe 14. The transponder may be pre-programmed by the manufacturer, or it may be encoded by the user, using a scanner read/write device.

A transponder is a radio transmitter-receiver activated for transmission of data by reception of a predetermined signal, and may also be referred to as a microtransponder, radiotransponder, radio tag, transceiver, etc. The signal comes from a dedicated scanner, which also receives and processes the data sent by the transponder in response to the signal. The scanner function can be combined with the write function, i.e. the process of encoding the data on the transponder. Such a combination instrument is called a scanner read/write device. An advantage of the transponder-scanner system stems from the fact the two units are not physically connected by wire, but are coupled inductively, i.e. by the use of electromagnetic radiation, typically in the range from 5–1,000 kHz, but also up to 1 GHz and higher.

Figure 3:
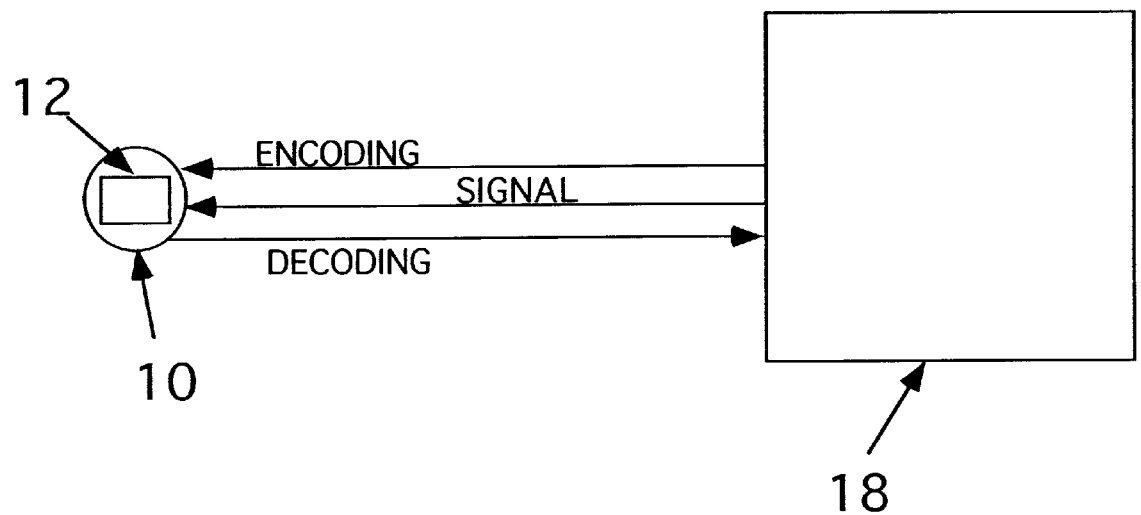
FIG. 3 is a schematic diagram of the signal pathway for encoding and decoding data on the transponders of the solid phase.

FIG. 3 is a flow chart illustrating the communication between the transponder 12 and a remote scanner read/write device 18. The transponder 12 associated with the solid phase beads 10 is encoded with data sent by electromagnetic waves from a remote scanner read/write device 18. After the assay steps are completed, the beads 10 are analyzed to detect the presence of a label indicative of binding of analyte and those that show the presence of the label are decoded. The scanner 18 sends a signal to the transponder 12. In response to the signal, the transponder 12 transmits the encoded data to the scanner 18.

Some transponders similar to those used in this invention are available commercially. Bio Medic Data Systems Inc. (BMDS, 255 West Spring Valley Ave., Maywood, N.J.) manufactures a programmable transponder for use in laboratory animal identification. The transponder is implanted in the body of an animal, such as a mouse, and is glass-encapsulated to protect the electronics inside the transponder from the environment. One of the transponders manufactured by this corporation, model# IPTT-100, has dimensions of 14×2.2×2.2 mm and weighs 120 mg. The transponder is user-programmable with up to 16 alphanumeric characters, the 16th letter programmable independently of the other 15 letters, and has a built-in temperature sensor as well. The electronic animal monitoring system (ELAMS) includes also a scanner read/write system to encode or read data on/from the transponder. The construction of the transponder and scanner is described in U.S. Pat. Nos. 5,250,944, 5,252,962 and 5,262,772, the disclosures of which are incorporated herein by reference. Other similar transponder-scanner systems include a multi-memory electronic identification tag (U.S. Pat. No. 5,257,011) manufactured by AVID Corporation (Norco, Calif.) and a system made by TEMIC-Telefunken (Eching, Germany). AVID's transponder has dimensions of 1 mm×1 mm×11 mm, and can encode 96 bits of information, programmed by the user. The present invention can be practiced with different transponders, which might be of different dimensions and have different electronic memory capacity.

The commercially available transponders are relatively large in size. The speed at which the transponders may be decoded is limited by the carrier frequency and the method of transmitting the data. In typical signal transmission schemes, the data are encoded by modulating either the amplitude, frequency or phase of the carrier. Depending on the modulation method chosen, compression schemes, transmission environment, noise and other factors, the rate of the signal transmission is within two orders of magnitude of the carrier frequency. For example, a carrier frequency of 1,000 Hz corresponds to rates of 10 to 100,000 bits per second (bps). At the rate 10,000 bps the transmission of 100 bits will take 0.01 sec. The carrier frequency can be several orders of magnitude higher than 1,000 Hz, so the transmission rates can be proportionally higher as well.

Therefore, the limiting factor in the screening process is the speed at which the transport mechanism carries the transponders through the read window of the fluorometer/scanner device. The rate of movement of small particles or cells is $10^4$–$10^5$ per second in state-of-the-art flow cytometers. A flow cytometer may be used to practice the present invention, if two conditions are met: (1) the transponders are small enough to pass through the flow chamber, and (2) the design of the flow chamber of the flow cytometer is modified to include an antenna for collecting the electromagnetic radiation emitted by transponders.

Figure 4:
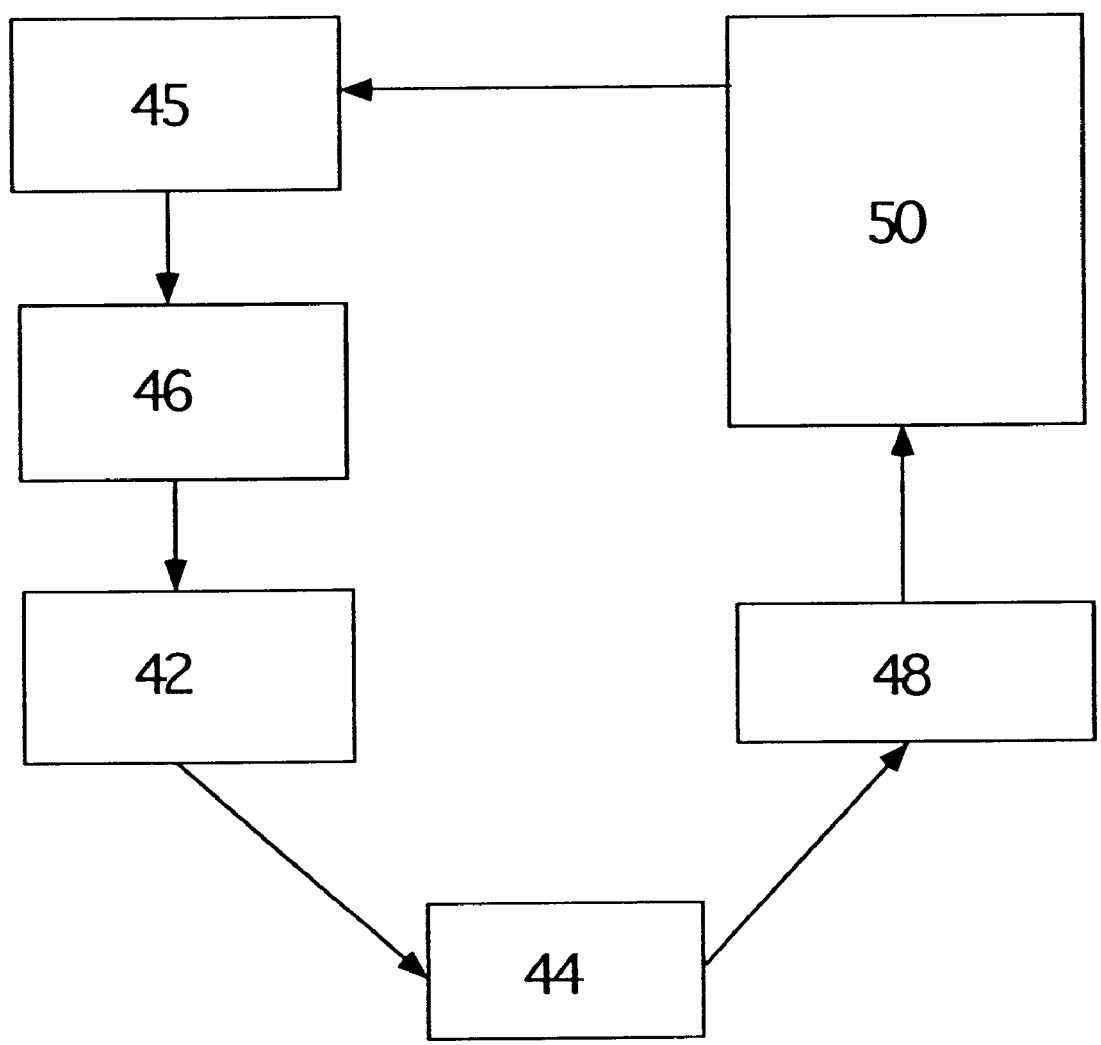
FIG. 4 is a schematic representation of a miniature transponder.
Figure 5:
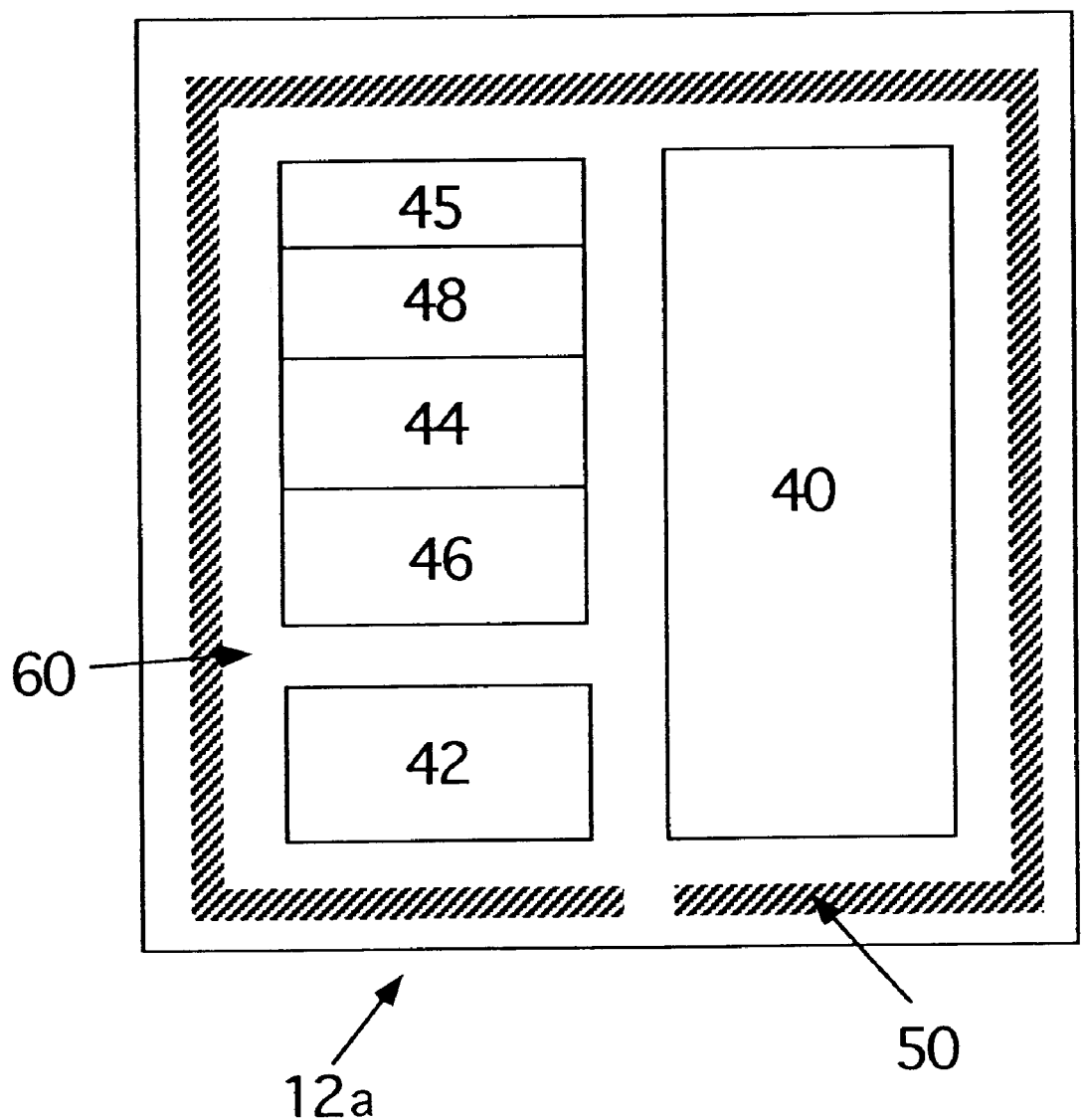
FIG. 5 is a plan view of a miniature transponder.

A miniature transponder is depicted in FIGS. 4 and 5. The source of the electrical power for the transponder 12a is at least one photovoltaic cell 40 within the transponder 12a, illuminated by light, preferably from a laser (not shown). The same light also induces the fluorescence of the fluorogenic molecules immobilized on the surface of the transponder 12a. The transponder 12a 9 includes a memory element 42 that may be of the EEPROM type. The contents of the memory is converted from the digital form to the analog form by a Digital-to-Analog converter 44 mounted on the transponder 12a. The signal is amplified by an amplifier 46, mixed with the carrier signal produced by an oscillator 48, and emitted to the outside of the transponder 12a by an antenna 50.

The contents of the transponder memory can be permanently encoded during the manufacturing process of the transponder, different batches of transponders being differently encoded. Preferably, the memory of the transponder is user-programmable, and is encoded by the user just before, during, or just after the biological material is deposited on the surface of the transponder. A user-programmable transponder 12a must have the "write" feature enabled by the antenna 50, amplifier 44 and the Analog-to-Digital converter 46 manufactured on the transponder 12a, as well as the dedicated scanner read/write device 27.

The advantages of the transponder of FIGS. 4 and 5 are several-fold. First, the dimension of the transponder is reduced, since most of the volume of current transponders is occupied by the solenoid. The design discussed above will enable the production of cubic transponders on the order of 0.01 to 1.0 mm along a side, preferably 0.05 to 0.2 mm.

Second, a large number of transponders can be manufactured on a single silicon wafer, and no further assembly would be required to attach the solenoid to the VLSI chip. As depicted schematically in FIG. 5, a silicon wafer 60 is simply cut to yield active transponders 12a. Third, the transponder, according the new design, will not need the glass capsule as an enclosure, further reducing the size of the transponder. Silicon dioxide ($SiO_2$) would constitute a significant portion of the surface of the transponder, and $SiO_2$ has chemical properties which are very similar to glass in terms of the feasibility of derivatization or immobilization of biomolecules. Alternatively, microtransponders may be coated with a variety of materials, including plastic, latex and the like.

Finally, most important, the narrow focus of the beam of the laser light would enable only one transponder to be active at a time, significantly reducing the noise level. Advanced user-programmability is desirable as well, various memory registers need to be addressable independently (writing in one register should not erase the contents of other registers).

Figure 6:
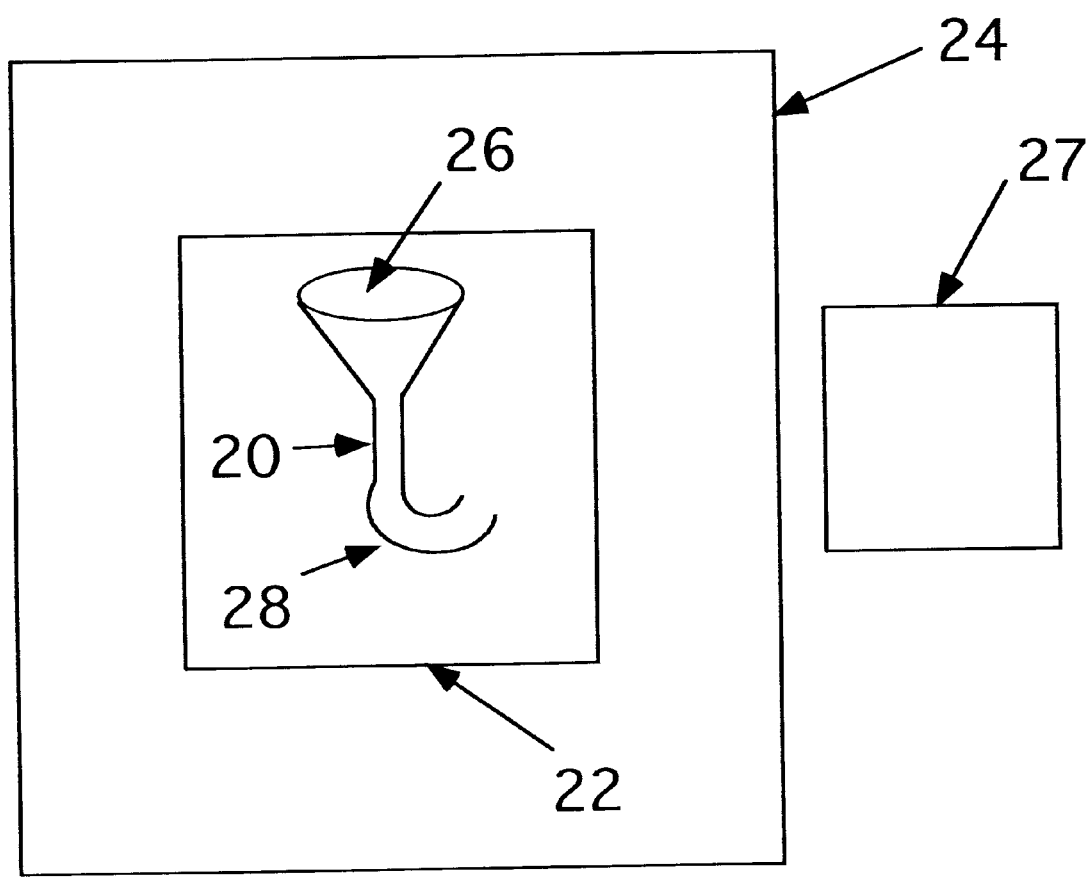
FIG. 6 is a plan view of a transport system/analytical instrument for implementing the present invention.
Figure 7:
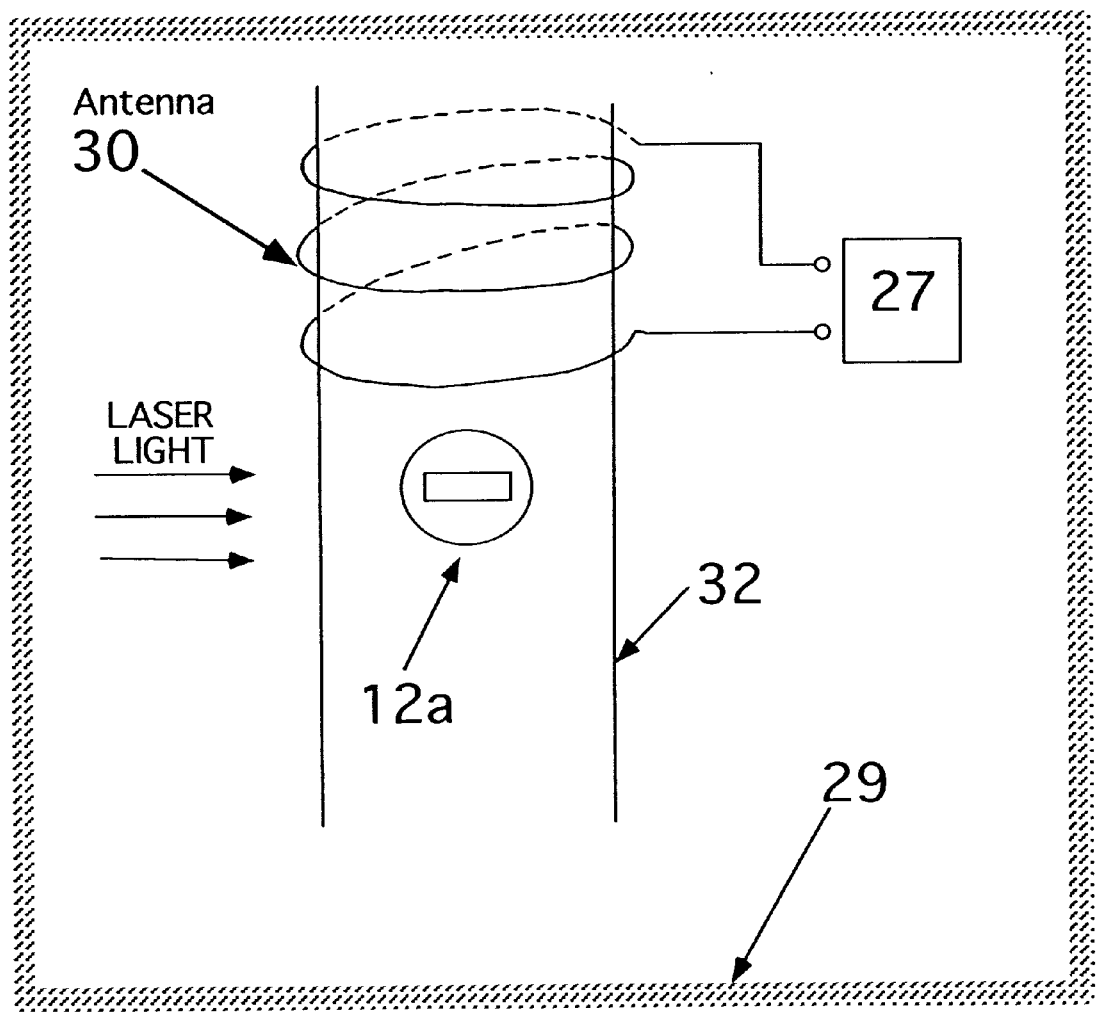
FIG. 7 is a plan view of a modified flow cytometer for high speed analysis of solid phase particles of the present invention.

FIG. 6 shows the analytical instrumentation and transport system used in an embodiment of the present invention. A quartz tube 20 is mounted in the readout window 22 of a fluorometer 24. The quartz tube 20 is connected to a metal funnel 26. The length of the quartz tube 20 is similar to the dimensions of the transponder 12. Transponders 12 are fed into the metal funnel 26, and pass from the funnel 26 into the quartz tube 20, where the fluorescence is read by the fluorometer 24 and the transponder 12 is decoded by the scanner 27, and then exit through a metal tube 28 and are conducted to a collection vessel (not shown). The metal funnel 26 and metal tube 28 are made of metal shield transponders 12 outside of the read window 22 by shielding from the electromagnetic signal from the scanner 27. This shielding prevents the scanner signal from reaching more than one transponder 12, causing multiple transponders 12 to be decoded.

Minimal modification of the fluorometer 24 would be needed in the vicinity of the location that the tube occupies at the readout moment to allow for positioning of the transponder reading device. To assure compatibility with existing assays, the glass surrounding the transponder could be coated with plastic currently used to manufacture beads.

In a preferred design, depicted in FIG. 4, a metal coil antenna 30 is wrapped around the flow cell 32 of a flow cytometer 29. The transponders 12 pass through the flow cell 32, and are decoded by the scanner device 27. The signal carrying the data sent from the transponders 12 is amplified by a first amplifier 34 and processed by the scanning device 27. As the transponders 12 are decoded, fluorescence from the transponders 12 is detected and analyzed by the flow cytometer 29.

In one embodiment of the present invention, multiple passes of the same set of transponders through the detector are implemented. The temperature is incrementally increased at each pass, the purpose being to gradually increase the stringency of binding, and to reduce effects of non-specific binding of the target to the probes on the transponders. After the detection step is completed, the transponders can be reconditioned for further use in another experiment by stripping the biomolecular coating chemically, and clearing the memory. If the target DNA is labeled with a fluorophore, an alternative to chemical stripping is the extensive wash at high temperature to dissociate and remove non-covalently bound target DNA.

Upon completion of the analysis step and decoding of the transponders, the data is analyzed to determine the sequence by correlating the sequence of the oligonucleotide probe immobilized on the transponder and the fluorescence readout of the transponder carrying the probe. The type of data related to the fluorescence readout may vary depending of the procedures used. If the target DNA is labeled with the fluorophore prior to annealing, or if the label is a single fluorophore, introduced in a chain extension reaction with a DNA polymerase after annealing, the fluorescence readout is simply the intensity of the fluorescence. Alternatively, if four ddNTPs are used with the purpose of identifying the nucleotide residue proximal to the 3' end of the probe or target DNA (depending on the design of the experiment), the fluorescence readout is both the intensity and the information about the wavelength of maximal fluorescence. The form of the data set is analogous to that yielded by sequencing by hybridization methods(SBH), and algorithms previously developed for SBH can also be used for digital sequencing (Drmanac R. et al., 1993, DNA Sequence Determination By Hybridization: A Strategy For Efficient Large-Scale Sequencing. Science 260, 1649–1652).

EXAMPLE 1

Immobilization Of DNA Probes On Transponders Using The Chemical Synthesis Of DNA Nucleic acids can be covalently linked to glass by direct chemical synthesis on a glass support. To prepare the support, 5'-dimethoxytrityl thymidine is reacted with one equivalent of tolylene-2,6-diisocyanate in the presence of one equivalent of N-ethyldiisopropylamine as a catalyst in pyridine/1,2-dichloroethane to generate the monoisocyanate. The monoisocyanate is not isolated, but is added directly to the alkylamine glass support, i.e. the aminopropyltriethoxysilane-derivatized glass surface of the transponders. The procedure is described in detail in B. S. Sproat and D. M. Brown, A New Linkage For Solid Phase Synthesis Of Oligodeoxyribonucleotides, Nucleic Acids Res. 13, 2979–2987, 1985. Such thymidine-derivatized support containing the stable nucleoside-urethane linkage is directly used for the chemical synthesis of oligodeoxynucleotides using a manual synthesis protocol on sintered funnels as described before (Caruthers, M. H. et al., Deoxyoligonucleotide synthesis via the phosphoramidite method. In: Gene Amplification and Analysis, Vol III (T. S. Papas et al., Eds.). Elsevier/North Holland, Amsterdam), using standard phosphoramidite-based DNA synthesis reagent. The thymidine-urethane linker is resistant to cleavage with base during the deprotection, and the resulting product is the deprotected oligonucleotide attached to the glass surface of the transponder through the urethane-thymidilate linker.

EXAMPLE 2

Determination Of The Sequence Of A Three Nucleotide Region Using AVID Transponders The target DNA is a single-stranded 50-residue long oligodeoxynucleotide. It is obtained from a PCR reaction using a 5'-fluoresceinated oligonucleotide as one of the primers, after linearly amplifying DNA. DNA used in the experiment is purified after PCR. Most of the sequence of 47 nucleotides in the 50 nt target is known, except for a region consisting of three residues, residue numbers 18–20, marked as NNN in the figure below:

The symbol "|" denotes the complementarity of nucleotides in the two sequences. There are exactly 64 possible sequences for 5'-GGTACTGCXXXACCTTCCA (SEQ ID NO:1), where X can be any nucleotide residue (A, C, G or T). 64 sets of AVID transponders are prepared, each set having a different oligonucleotide probe (upper sequence in the figure above) synthesized on the surface of the transponder using standard phosphoramidite chemistry as described in Example 1. The linker has the (dT)$_{10}$ sequence to facilitate annealing. The transponders are electronically encoded with a number 1 through 64, the number corresponding to the sequence of the oligonucleotide bound to the transponder. 64 transponders, each from a different set, are put into a 10 ml vessel. A solution containing the target (5 ml volume) is then added to the vessel, the contents of the vessel is heated to 95° C., cooled slowly over the period of 10 min to the experimentally predetermined wash temperature $T_{wash}$ ($T_{wash}$ can range from room temperature to 60° C., data not shown). After the annealing step, the transponders were extensively washed at temperature $T_{wash}$, and then stored in a buffer at room temperature.

Each of the 64 transponders was subjected to both fluorescence measurement and electronic decoding of the tag. As a result, each of 64 possible sequences was associated with a number, fluorescence readout, that indicated whether the template had annealed to the oligonucleotide on the transponder, thus providing the information about the sequence of the 3 nt region.

EXAMPLE 3

Determination Of The Sequence Of A Two Nucleotide Region Using Combinatorial Oligonucleotide Synthesis On BMDS Transponders The target was a single-stranded 50-residue long oligonucleotide. It was obtained from a PCR reaction using a 5'-fluoresceinated oligonucleotide primer, after linearly amplifying DNA. DNA used in the experiment is purified after PCR. Most of the sequence of 48 nucleotides in the 50 nt template was known, except for the region of two residues, residue numbers 18–19, marked as NN in the figure below:

chemistry to sequentially synthesize the following residues: TTTTTTTTTTGGTACTGCA-3(SEQ ID NO:5). The transponders are split into four groups of approximately equal numbers (i.e. 50). Each of the four groups is subjected to a single cycle of solid phase oligonucleotide synthesis with a different nucleotide phosphoramidite. That is, transponders from group 1 are derivatized with adenosine phosphoramidite (A), group 2—cytosine phosphoramidite (C), group 3—guanosine phosphoramidite (G), and group 4—thymidine phosphoramidite (T). The volume of each of the four condensations is about 4 ml. After completing the first cycle, the 4 groups are subjected to electronic encoding with the residue abbreviations given above. Thus, the first alphanumeric character indicates which condensation takes place in the first cycle of combinatorial synthesis. Then, all the transponders are pooled together and mixed thoroughly, and then split into new four groups having approximately the same number of transponders. These four new groups are subjected to the second combinatorial coupling step. The scheme for the second coupling is identical to that of the first coupling. Electronic encoding after the second cycle adds a second alphanumeric character, corresponding to the nucleoside coupled in the second synthesis cycle. As a result, each transponder is encoded with two alphanumeric characters which identify the sequence of two nucleotide residues at the 3' end of the oligonucleotide attached to the surface of the transponder. The transponders having oligonucleotides coupled to their surfaces are immersed in a 20 ml vessel in the solution containing the template, the contents of the vessel is heated to 95° C., cooled slowly over the period of 10 min to the experimentally predetermined annealing temperature $T_{ann}$ ($T_{ann}$ can range from room temperature to 60° C., data not shown). After the annealing step, the transponders are extensively washed at temperature $T_{ann}$. The fluorescence of individual transponders is recorded and the transponder memories are decoded. Strong fluorescence indicates that the complement of the dinucleotide sequence bound to the transponder is present in the target.

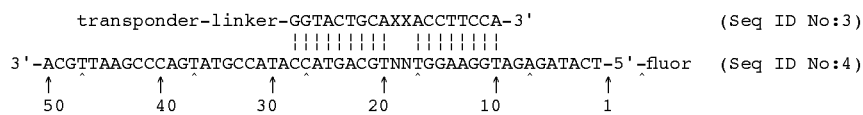

```
    transponder-linker-GGTACTGCAXXACCTTCCA-3'                      (Seq ID No:3)
                       |||||||||  ||||||||
3'-ACGTTAAGCCCAGTATGCCATACCATGACGTNNTGGAAGGTAGAGATACT-5'-fluor    (Seq ID No:4)
   ↑         ↑         ↑         ↑         ↑         ↑
   50        40        30        20        10        1
```

0

The symbol "|" denotes the complementarity of nucleotides in the two sequences. The linker has the (dT)$_{10}$ sequence to facilitate annealing. There are exactly 16 possible sequences of oligonucleotides 5'-GGTACTGCAXXACCTTCCA (SEQ ID NO:3), where X can be any nucleotide residue (A, C, G or T). These sequences are synthesized in a combinatorial fashion on 200 BMDS transponders (14×2×2 mm, volume of each transponder is about 50 μl) as follows. First, the underivatized glass surface of the transponders is treated as described in Example 1 to introduce the functional hydroxy groups on the surface of transponders. Then, the transponders are subjected to 18 rounds of solid phase oligonucleotide synthesis using standard phosphoramidite

EXAMPLE 4

Determination Of The Sequence Of A Three Nucleotide Region Using A Single-Nucleotide Extension By DNA Polymerase The target was a single-stranded 50-residue long oligonucleotide obtained from a PCR reaction after linearly amplifying DNA. The target DNA does not carry any fluorophore label. Most of the sequence of 47 nucleotides in the 50 nt target is known, except for the region of three residues, residue numbers 18–20, marked as NNN in the figure below:

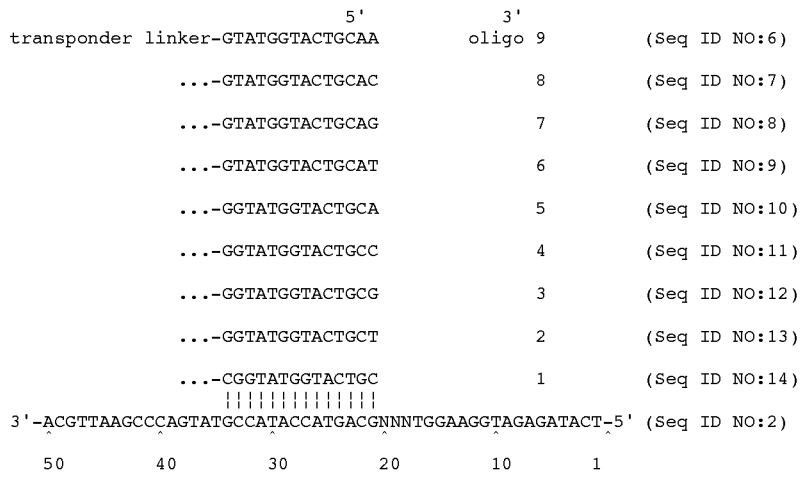

The symbol "|" denotes the complementarity of nucleotides in the two sequences. The linker has the $(dT)_{10}$ sequence to facilitate annealing. Nine groups of five AVID transponders are derivatized by the chemical synthesis of oligonucleotides 1 through 9 as shown in the figure above, and electronically encoded with numbers 1 through 9, respectively. The transponders are placed in one 5 ml vessel, and 2 mls of the solution containing the target (final concentration 10 nM to 10 µM) is added to the vessel. The contents of the vessel are heated to 95° C., cooled slowly over the period of 10 min to the experimentally predetermined extension temperature $T_{ex}$ ($T_{ex}$ can range from room temperature to 60° C., data not shown). After the annealing step, the transponders are extensively washed at temperature $T_{ex}$. DNA polymerase and four dideoxynucleotide triphosphates, ddATP, ddCTP, ddGTP and ddTTP (obtained from Applied Biosystems) derivatized with four different fluorophores, such as those used in Applied Biosystems automated sequencers are then added to the vessel, and the vessel is incubated at $T_{ex}$ for 15 minutes. Subsequently, the transponders are extensively washed at the wash temperature $T_{wash}$. A set of data points, each in the form of (oligonucleotide$_{13}$sequence, fluorescence_intensity, wavelength_of_maximum_fluorescence), is obtained. For highly fluorescent transponders, the wavelength of maximum fluorescence indicates the residue type, and the number encoded on the transponder indicates the position of the residue in the chain, thus defining the sequence of the 3 nt region of the target.

---

I claim:

1. A solid phase support comprising:
   (a) a transponder which is a monolithic integrated circuit which can transmit via electromagnetic radiation data stored within said integrated circuit; and
   (b) an oligonucleotide probe attached to the surface of the integrated circuit, wherein said probe is capable of binding to a nucleic acid.

2. A solid phase support comprising:
   (a) a transponder which is a monolithic integrated circuit which can transmit via electromagnetic radiation data stored within said integrated circuit;
   (b) at least one layer of a coating deposited on the surface of the integrated circuit, (c) an oligonucleotide probe attached to the coating layer, wherein said probe is capable of binding to a target nucleic acid.

3. The solid phase support of claim 1, wherein said monolithic integrated circuit comprises a photovoltaic cell that can be activated by light.

4. The solid phase support of claim 3, wherein said data stored in the memory of said monolithic integrated circuit are encoded by a manufacturer of said integrated circuit.

5. The solid phase support of claim 4, wherein said data stored in the memory of the monolithic integrated circuit are encoded by a user with a scanner device.

6. The solid phase support of claim 2, wherein said monolithic integrated circuit comprises (a) a photovoltaic cell that can be activated by light and (b) said coating is at least partially transmissible to light.

7. The solid phase support of claim 6, wherein said data stored in the memory of said monolithic integrated circuit are encoded by a manufacturer of said integrated circuit.

8. The solid phase support of claim 7, wherein said data stored in said memory of the monolithic integrated circuit are encoded by a user with a scanner device.

9. A kit for determining the sequence of target nucleic acids in a sample, comprising:
   (a) at least one assay vessel, containing at least one solid phase particle having (i) a transponder and (ii) an oligonucleotide probe bound to its surface; and
   (b) at least one label reagent.

10. The kit of claim 9, wherein the label reagent comprises a reagent that labels the target nucleic acid.

11. The kit of claim 9, wherein the label reagent comprises a labeled nucleotide.

12. The kit of claim 9, further comprising:
    (a) a sample diluent buffer solution; and
    (b) an enzyme reaction buffer solution.

13. A kit of claim 9, wherein the transponder is a monolithic integrated circuit.

14. The kit of claim 13, wherein the label reagent comprises a reagent that labels the target nucleic acid.

15. The kit of claim 13, wherein the label reagent comprises a labeled nucleotide for use in a chain extension reaction using DNA polymerase.

16. The kit of claim 13, further comprising:
    (a) a sample diluent buffer solution; and
    (b) an enzyme reaction buffer solution.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GGTACTGCNN NACCTTCCA                                                19

(2) INFORMATION FOR SEQ ID NO:2:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TCATAGAGAT GGAAGGTNNN GCAGTACCAT ACCGTATGAC CCGAATTGC         50

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGTACTGCAN NACCTTCCA         19

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TCATAGAGAT GGAAGGTNNT GCAGTACCAT ACCGTATGAC CCGAATTGC         50

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TTTTTTTTTT GGTACTGCA         19

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTATGGTACT GCAA         14

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

-continued

GTATGGTACT GCAC                                                              14

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTATGGTACT GCAG                                                              14

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTATGGTACT GCAT                                                              14

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGTATGGTAC TGCA                                                              14

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGTATGGTAC TGCC                                                              14

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGTATGGTAC TGCG                                                              14

(2) INFORMATION FOR SEQ ID NO:13:

```
        (i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GGTATGGTAC TGCT                                                            14

(2) INFORMATION FOR SEQ ID NO:14:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

CGGTATGGTA CTGC                                                            14
```